(12) United States Patent
Taborga Claure et al.

(10) Patent No.: US 12,145,136 B2
(45) Date of Patent: Nov. 19, 2024

(54) CONVERSION OF HEAVY AROMATICS TO LIGHTER AROMATICS WITH LOW RING SATURATION AND HYDROCARBON CRACKING

(71) Applicant: ExxonMobil Technology and Engineering Company, Annandale, NJ (US)

(72) Inventors: Micaela Taborga Claure, Miami, FL (US); Doron Levin, Highland Park, NJ (US); Joseph E. Gatt, Annandale, NJ (US); Scott Weigel, Allentown, PA (US); Pedro M. Serna Merino, Branchburg, NJ (US)

(73) Assignee: EXXONMOBIL TECHNOLOGY AND ENGINEERING COMPANY, Spring, TX (US)

( * ) Notice: Subject to any disclaimer, the term of this patent is extended or adjusted under 35 U.S.C. 154(b) by 201 days.

(21) Appl. No.: 17/907,748

(22) PCT Filed: Feb. 19, 2021

(86) PCT No.: PCT/US2021/018700
§ 371 (c)(1),
(2) Date: Sep. 29, 2022

(87) PCT Pub. No.: WO2021/216176
PCT Pub. Date: Oct. 28, 2021

(65) Prior Publication Data
US 2023/0135668 A1 May 4, 2023

(51) Int. Cl.
*B01J 29/035* (2006.01)
*B01J 29/00* (2006.01)
*C10G 45/54* (2006.01)

(52) U.S. Cl.
CPC ......... *B01J 29/035* (2013.01); *B01J 29/005* (2013.01); *C10G 45/54* (2013.01); *C10G 2400/28* (2013.01); *C10G 2400/30* (2013.01)

(58) Field of Classification Search
CPC ........ B01J 29/005; B01J 29/035; B01J 29/18; B01J 29/185; B01J 29/22; B01J 29/40;
(Continued)

(56) References Cited

U.S. PATENT DOCUMENTS 6,867,340 B2    3/2005   Oh et al. ................. 585/475
7,626,064 B1   12/2009   Boldingh et al. ......... 585/475
(Continued)

FOREIGN PATENT DOCUMENTS

CN      108014842 A  *  5/2018   .............. B01J 29/80
WO    WO2017/202495      11/2017

OTHER PUBLICATIONS

Machine translation of CN108014842. (Year: 2018).*
(Continued)

*Primary Examiner* — Brian A McCaig
(74) *Attorney, Agent, or Firm* — Shook, Hardy & Bacon L.L.P.

(57) ABSTRACT

A catalyst may include a metallic function derived from a metal constrained within cages and/or channels of a microporous material, wherein the cages and/or channels of the microporous material are defined by 8 tetrahedral atoms or fewer; and an acidic function derived from an additional zeolite having cages and/or channels defined by 10 or more tetrahedral atoms, wherein the microporous material providing the metallic function and additional zeolite providing the acidic function are coupled by a binder.

24 Claims, 1 Drawing Sheet

(58) Field of Classification Search
CPC ........ B01J 29/405; B01J 29/44; B01J 29/743; B01J 29/80; B01J 35/19; B01J 35/40; B01J 37/088; B01J 37/18; B01J 2229/186; C07C 6/126; C07C 15/08; C07C 2529/18; C07C 2529/40; C07C 2529/74; C07C 2529/80; C10G 11/02; C10G 45/04; C10G 45/54; C10G 69/04; C10G 2400/28; C10G 2400/30
See application file for complete search history.

(56) References Cited

U.S. PATENT DOCUMENTS

| | | | |
|---|---|---|---|
| 8,183,424 B2 | 5/2012 | Levin et al. | 585/323 |
| 10,058,853 B2 | 8/2018 | Lai et al. | 585/475 |
| 10,118,165 B2 | 11/2018 | Lai et al. | 585/475 |
| 2022/0126278 A1 | 4/2022 | Peer et al. | B01J 29/40 |

OTHER PUBLICATIONS

U.S. Appl. No. 62/909,864, filed Oct. 3, 2019, Taborga Claure, Micaela et al.

Moliner, M. et al. (2016) "Reversible Transformation of Pt Nanoparticles into Single Atoms Inside High-Silica Chabazite Zeolite," *Jrnl. Amer. Chem. Soc.*, v.138(48), p. 15743-15750.

Paolucci, C. et al. (2017) "Dynamic Multinuclear Sites Formed by Mobilized Copper Ions in NOx Selective Catalytic Reduction," *Science*, v.357(6354), pp. 898-903.

\* cited by examiner

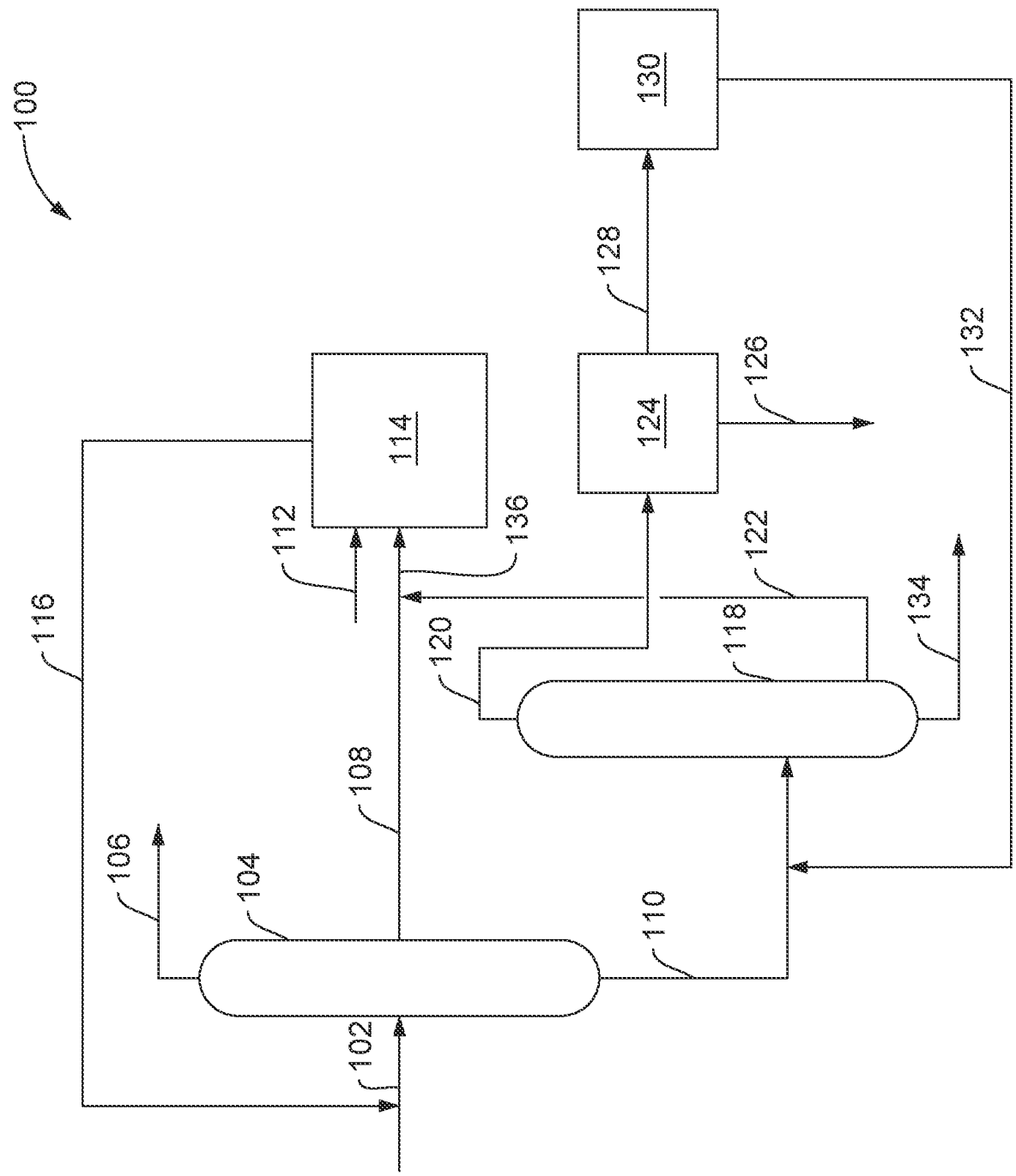

CONVERSION OF HEAVY AROMATICS TO LIGHTER AROMATICS WITH LOW RING SATURATION AND HYDROCARBON CRACKING

FIELD

This application relates to a catalyst system for converting C9+ aromatics to lighter aromatics, and, more particularly, embodiments relate to a catalyst system configured to hydrogenate light olefins generated from in-situ elimination of C2+ alkyl groups from C9+ aromatics.

BACKGROUND

In the refining and petrochemical industry, benzene, toluene, and xylenes are often produced on-purpose as feedstocks for downstream chemical processes. Benzene, toluene, and xylenes may sometimes be referred to by the initials BTX and are an important feedstock for the production of styrene, phenolic resins, polycarbonates, nylons, polyurethanes, polyesters, and motor fuels, for example. BTX may be produced by several chemical processes such as catalytic reforming of naphtha and stream cracking of naphtha. However, the quantity of xylene available from reforming and stream cracking is limited and so solutions have been derived for the production of xylene by transalkylation of C9+ aromatic hydrocarbons with benzene and/or toluene over noble metal-containing zeolite catalysts. However, during the transalkylation of C9+ aromatics with, for example, toluene to produce xylene and benzene, saturated by-products, which boil in the same temperature range as the desired aromatic products may be produced making separation of the desired products at high purity levels difficult. The saturated by-products may be a result of hydrogenation of the C6+ aromatics produced via the transalkylation, dealkylation, and hydrogenation chemistries, for example. A commercial benzene product specification may require a purity of 99.85 wt. % or greater. However, initial benzene purity after distillation of a transalkylation reaction product may be in the range of about 99.2 wt. % to 99.5 wt. % due to the presence of co-boiling species, such as methylcyclopentane, cyclohexane, methylcyclohexane, 2,3-dimethylpentane, dimethylcyclopentane and 3-methylhexane. Therefore, an additional extraction step is usually required to further improve benzene product purity to the desired level.

Further, as refineries and chemical plants have focused on the production of benzene and xylenes by transalkylation of lower value C9+ aromatics with benzene or toluene to produce xylene, several challenges have emerged. Chemical plants would ideally like to process as much of the heavy $C_9$+ aromatics as possible while minimizing and potentially removing the toluene/benzene co-feed. Both transalkylation activity and dealkylation activity are important for a successful catalyst system. Transalkylation is the ability to transalkylate methyl groups to form xylenes. Dealkylation is the ability to dealkylate ethyl, propyl, and butyl groups present on the $C_9$+ aromatics to allow the formation of lower methyl/ring species that may transalkylate with higher methyl/ring species to form xylenes. A metal function on the catalyst is required to saturate olefins formed during dealkylation while minimizing aromatic saturations. As plants move to increased amounts of $C_9$+ in the feed, acceptable activity and catalyst life become challenging.

The lifetime of transalkylation catalysts is strongly dependent on the presence in the feed of aromatic compounds having alkyl substituents with two or more carbon atoms, such as ethyl and propyl groups. Such feed components tend to undergo disproportionation to produce $C_{10}$+ coke precursors at operating conditions. Unsaturated species liberated by dealkylation may be further reacted with the transalkylation catalyst which may produce a carbon deposit that blocks accessibility of other reactants to reach active sites on the catalyst. A solution may be to perform in-situ elimination of the unsaturated species through hydrogenation. Ideally, a hydrogenation catalyst may fully saturate the unsaturated species to the corresponding alkane while minimizing ring saturation of the aromatic components. However, problems exist with catalyst selectivity at operating conditions which can cause hydrogenation of the aromatic species thereby reducing yields and further increasing separation difficulty. While noble metals on zeolite/binder blends may be the primary catalyst choice for hydrogenation activities, metals such as Pt typically cannot selectively remove olefins without causing some degree of ring saturation. One solution may be to add additional metals to the catalyst that reduce hydrogenation of aromatic rings, however such catalysts containing more than one metal typically show lower overall catalytic activity and may still generate product species with a degree of ring saturation.

SUMMARY

This application relates to a catalyst system for converting C9+ aromatics to lighter aromatics, and, more particularly, embodiments relate to a catalyst system configured to hydrogenate light olefins generated from in-situ dealkylation of C2+ alkyl species from C9+ aromatics while minimizing the hydrogenation of desired BTX products.

Disclosed herein is catalyst comprising: a metallic function derived from a metal constrained within cages and/or channels of a microporous material, wherein the cages and/or channels of the microporous material are defined by 8 tetrahedral atoms or fewer; and an acidic function derived from an additional zeolite having cages and/or channels defined by 10 or more tetrahedral atoms, wherein the microporous material providing the metallic function and additional zeolite providing the acidic function are coupled by a binder.

Further disclosed herein is a method comprising: introducing a feed comprising hydrogen, toluene, and C9+ aromatic hydrocarbons into a reactor, wherein at least a portion of the C9+ aromatic hydrocarbons comprise a C2+ alkyl group; and contacting the feed with a catalyst comprising: a metallic function derived from a metal constrained within cages and/or channels of a microporous material, wherein the cages and/or channels of the microporous material are defined by 8 tetrahedral atoms or fewer; and an acidic function derived from an additional zeolite having cages and/or channels defined by 10 or more tetrahedral atoms, wherein the microporous material providing the metallic function and additional zeolite providing the acidic function are coupled by a binder, wherein the catalyst is effective to dealkylate at least a portion of the C9+ aromatic hydrocarbons comprising a C2+ alkyl group to generate a corresponding olefin and C9+ aromatic hydrocarbon and hydrogenate at least a portion of the corresponding olefin to form a corresponding alkane.

Further disclosed herein is a method comprising: contacting an aromatic hydrocarbon feed with a catalyst composition comprising: a metallic function derived from a metal constrained within cages or channels of a microporous material, wherein the cages or channels of the microporous material are defined by 8 tetrahedral atoms or fewer; and an acidic function derived from an additional zeolite having channels defined by 10 or more tetrahedral atoms, wherein the microporous material providing the metallic function and additional zeolite providing the acidic function are coupled by a binder, wherein the aromatic hydrocarbon feed comprises toluene, and C9+ aromatic hydrocarbons, and wherein at least a portion of the C9+ aromatic hydrocarbons comprise a C2+ alkyl group; dealkylating at least a portion of the C9+ aromatic hydrocarbon comprising C2+ alkyl groups to form a corresponding C2+ olefin and C9+ aromatic hydrocarbon; saturating at least a portion of the C2+ olefin formed to produce a corresponding C2+ alkane; and transalkylating at least a portion of the C9+ aromatic hydrocarbon with the toluene to form xylene. Xylene.

BRIEF DESCRIPTION OF THE DRAWINGS

These drawings illustrate certain aspects of the present invention and should not be used to limit or define the invention.

The FIGURE is a schematic diagram illustrating an embodiment of a transalkylation process.

DETAILED DESCRIPTION

This application relates to a catalyst system for converting C9+ aromatics to lighter aromatics, and, more particularly, embodiments relate to a catalyst system configured to hydrogenate light olefins generated from in-situ dealkylation of C2+ alkyl species from C9+ aromatics while minimizing ring loss of desired BTX products. While the methods and systems disclose herein may be suitable in a standalone unit, the methods and systems may be particularly suitable for an integrated process within a refinery or chemical plant.

As discussed above, a common source of BTX in refineries and chemical plants may be from reaction of a naphtha feedstock. The naphtha feedstock may be reacted to form a C6+ aromatic stream that comprises benzene, toluene, and xylenes, as well as alkyl substituted aromatic species thereof. However, the process described herein may be utilized with any C6+ aromatic stream. In some examples, the present disclosure may refer to C6+, C7+, C8+, and C9+ streams and components. As used herein the term "Cn+", wherein n is a positive integer, means a compound or group containing at least n carbon atoms. In addition, the term "Cn+ aromatics", wherein n is a positive integer, means that a stream or stream component comprising aromatic hydrocarbons having at least n number of carbon atom(s) per molecule. For example, a C6+ stream may include molecules with 6 or more carbon atoms per molecule such as 6, 7, 8, 9, 10, or more carbons and a C9+ stream may include molecules with 9 or more carbon atoms per molecule such as 9, 10, or more carbons. The exact composition a C6+ stream may depend on the composition of reacted naphtha and the process condition under which the naphtha is reacted. Some specific C6+ aromatic compounds may include, without limitation, benzene, toluene, xylene, 1,3,5-trimethylbenzene, 1,2,4,5-tetramethylbenzene, 1,2,4-trimethylbenzene, 1,2,4-trimethylbenzene, ethyltoluenes, ethylxylenes, propyl-substituted benzenes, butyl-substituted benzenes, and dimethylethylbenzenes, for example. In addition to the catalytic reforming and steam cracking processes described earlier, C6+ aromatics may be sourced from any refinery process that is rich in aromatics, such as FCC naphtha or TCC naphtha.

A process for producing xylene by transalkylation of a C9+ aromatic hydrocarbon feedstock with a C6 and/or C7 aromatic hydrocarbon may include: (a) contacting a C9+ aromatic hydrocarbon feedstock, at least one C6 and/or C7 aromatic hydrocarbon, and hydrogen with a catalyst under conditions effective to dealkylate at least a portion of the C9+ aromatic hydrocarbons in the feedstock containing C2+ alkyl groups to form the corresponding C9+ aromatic hydrocarbon and corresponding C2+ olefin, saturate the C2+ olefins formed, and transalkylate C9+ aromatic hydrocarbons with at least one C6-C7 aromatic hydrocarbon to form an effluent comprising xylene.

The FIGURE illustrates an exemplary process 100 where a C9+ aromatic feed is transalkylated to form xylene. Process 100 may start by introducing feed 102 comprising C6+ hydrocarbons into fractionator 104. Feed 102 may include any of the C6+ hydrocarbons disclosed herein, for example. In fractionator 104, the hydrocarbons in feed 102 may be fractionated to produce a benzene product stream 106 which may include a majority of benzene present in feed 102. Fractionator 104 may further fractionate feed 102 into toluene stream 108 and C9+ stream 110. Toluene stream 108 may include a majority of the toluene present in feed 102 and C9+ stream 110 may include a majority of the C9+ components in feed 102. While fractionator 104 is illustrated in the FIGURE as a single distillation column, fractionator 104 may include a distillation train of including a plurality of distillation columns to generate benzene product stream 106, toluene stream 108, and C9+ stream 110.

From fractionator 104, C9+ stream 110 may be combined with xylene recycle stream 132 and introduced into fractionator 118. The feed to fractionator 118 may include the majority of C9+ compounds from feed 102 as well as a majority of the recycled xylenes from xylene isomerization unit 130, as will be described below. Fractionator 118 may separate components to generate xylene rich stream 120, C9+ aromatics stream 122, and, optionally, C11+ aromatics stream 134. Xylene rich stream 120 may contain a majority of the C8 and lighter hydrocarbons from the feed to fractionator 118. C9+ aromatics stream 122 may contain a majority of hydrocarbons with carbon numbers ranging from C9 to C10 from the feed to fractionator 118. C11+ aromatics stream 134 may contain the balance of hydrocarbons fed to fractionator 118 and may contain hydrocarbons with carbon numbers of C11+. While fractionator 118 is illustrated in the FIGURE as a single distillation column, fractionator 118 may include a distillation train of including a plurality of distillation columns to generate xylene rich stream 120, C9+ aromatics stream 122, and, C11+ aromatics stream 134.

From fractionator 118, xylene rich stream 120 may be introduced into xylene separation unit 124 which may include equipment to separate xylene rich stream 120 into xylene product stream 126. Xylene product stream 126 may include separate product streams for o-xylene, m-xylene, and p-xylene. Distillation or other separation unit operations may be used to separate o-xylene, m-xylene, and p-xylene streams which may then be utilized in downstream processes, for example. As p-xylene is generally the more desired isomer, additional chemical processes may be used to increase yield of p-xylene. In some examples, a xylene isomerization stream 128 comprising o-xylene and m-xylene may be recovered in xylene separation unit 124 and introduced into xylene isomerization unit 130 which may contain a reactor containing a catalyst capable of catalyzing xylene isomerization. Xylene recycle stream 132 exiting xylene isomerization unit 130 may include a mixture of o-xylene, m-xylene, and p-xylene.

From fractionator 118, C9+ aromatics stream 122 may be combined with toluene stream 108 to form heavy aromatic stream 136 which may be introduced into transalkylation unit 114.

Transalkylation unit 114 may include a reactor with a catalyst, such as those catalysts described herein, that is capable of catalyzing a dealkylation reaction of aromatic hydrocarbons containing $C_2+$ alkyl groups and to saturate $C_2+$ olefins formed. The catalysts utilized in transalkylation unit 114 may further effective to transalkylate C9+ aromatic hydrocarbons with a C6-C7 aromatic hydrocarbon to generate xylene. Hydrogen stream 112 may be introduced into transalkylation unit 114 to provide a hydrogen source for saturating C2+ olefins formed during dealkylation. Transalkylation effluent stream 116 from transalkylation unit 114 may be combined with feed 102 before introduction into fractionator 104. Transalkylation effluent stream 116 may include benzene, toluene, and mixed xylenes as well as unreacted C9+ aromatic hydrocarbons, for example.

The transalkylation unit 144 may include a single bed catalyst system or may include a multi-bed catalyst system for producing xylene. The catalyst system may include at least one, two, or optionally three, catalyst beds which are arranged so that a first catalyst bed may be located upstream of the second catalyst bed and, if present, the third catalyst bed may be located downstream of the second catalyst bed, when the catalyst system is brought into contact with heavy aromatic stream 136. The first catalyst bed including a first catalyst may be effective to dealkylate aromatic hydrocarbons in heavy aromatic stream 136 containing $C_2+$ alkyl groups and to saturate the resulting $C_2+$ olefins, whereas the second catalyst bed is effective to transalkylate C9+ aromatic hydrocarbons with C7-C8 aromatic hydrocarbons to produce xylenes. The optional third catalyst bed may be effective to crack non-aromatic cyclic hydrocarbons in effluent from the first and second catalyst beds.

The transalkylation unit may be operated at a temperature ranging from about 32° F. (0° C.) to about 1110° F. (600° C.). Alternatively, the transalkylation unit may be operated at a temperature ranging from about 32° F. (0° C.) to about 100° F. (38° C.), about 100° F. (38° C.) to about 200° F. (93° C.), about 200° F. (93° C.) to about 300° F. (149° C.), about 300° F. (149° C.) to about 400° F. (204° C.), about 400° F. (204° C.) to about 500° F. (260° C.), about 500° F. (206° C.) to about 600° F. (316° C.), about 600° F. (316° C.) to about 700° F. (371° C.), about 700° F. (371° C.) to about 800° F. (427° C.), about 800° F. (427° C.) to about 900° F. (482° C.), about 900° F. (482° C.) to about 1000° F. (538° C.), or about 1000° F. (538° C.) to about 1110° F. (599° C.). The transalkylation unit may operate at any pressure ranging from about atmospheric (14.7 psia 101.325 kPa) to about 1400 psi (6952 kPa). Alternatively, the transalkylation unit may operate at a pressure ranging from about 14.7 psi (101.325 kPa) to about 250 psi (1725 kPa), about 250 psi (1725 kPa) to about 500 psi (3447 kPa), about 500 psi (3447 kPa) to about 750 psi (5171 kPa), about 750 psi (5171 kPa) to about 1000 psi (6895 kPa), about 1000 psi (6895 kPa) to about 1200 psi (8274 kPa), or about 1200 psi (8274 kPa) to about 1400 psi (9653 kPa).

The catalyst may include a metallic function derived from a metal constrained within cages or channels of a microporous material and an acidic function derived from an additional zeolite. The acidic function of the zeolite may enable the catalyst to catalyze dealkylation reactions such as dealkylation of aromatic hydrocarbons containing $C_2+$ alkyl groups to the corresponding aromatic hydrocarbon and $C_2+$ olefin. The metallic function may enable the catalyst to catalyze hydrogenation reactions such as the hydrogenation of $C_2+$ olefins to their corresponding alkane. The cages or channels of the microporous material may be defined by 8 tetrahedral atoms or fewer. As will be shown in greater detail below, microporous materials comprising cages or channels of 8 tetrahedral atoms or fewer may exhibit size exclusionary properties whereby relatively larger molecules are unable to diffuse into the microporous material to react with the metal function. The size exclusion may yield greater selectivity of hydrogenating $C_2+$ olefins generated from dealkylation of aromatic hydrocarbons containing $C_2+$ alkyl groups and reduced selectivity to hydrogenate aromatic rings. In some examples, the additional zeolite may have channels defined by 10 or more tetrahedral atoms. In further examples, the microporous material and additional zeolite may be coupled by a binder.

The microporous material may include any material that comprises cages or channels that may be defined by 8 tetrahedral atoms and/or with cages or channels defined by a kinetic diameter of 5.85 Angstroms or smaller which may be the largest measurement of the cages or channels. Some suitable microporous materials may include, but are not limited to, AEI, AFT, AFX, CHA, CDO, DDR, EDI, ERI, IHW, ITE, ITQ-55, ITW, KFI, MER, MTF, MWF, LEV, LTA, PAU, PWY, RHO, SOD, SFW, UFI, and combinations thereof. The microporous material may include a metal such as a metal selected from Groups 6 to 12 of the Periodic Table of the Elements where the metal is at least partially disposed within the cages or channels of the microporous material. Some exemplary metals may include, but are not limited to, platinum, palladium, gallium, iridium, rhenium, copper, silver, gold, ruthenium, rhodium, iron, tungsten, molybdenum, cobalt, nickel, and combinations thereof. In some examples, two metals may be selected where the second metal is chosen to have a lower benzene saturation activity than the first metal. The metal may be present in the catalyst in an amount between about 0.001 wt. % and about 5 wt. % of the catalyst. Alternatively, the metal may be present in an amount of about 0.001 wt. % to about 0.010 wt. %, about 0.010 wt. % to about 0.1 wt. %, about 0.1 wt. % to about 1 wt. %, or about 1 wt. % to about 5 wt. % of the catalyst. Further, the microporous material may be present in any suitable amount in the catalyst. For example, the microporous material may be present in an amount of about 1 wt. % to about 90 wt. % by weight of the catalyst. Alternatively, the microporous material may be present in an amount of about 1 wt. % to about 10 wt. %, about 10% to about 30 wt. %, about 30 wt. % about 50 wt. %, about 50 wt. % to about 70 wt. %, about 70 wt. % to about 90 wt. %, or any ranges therebetween.

The additional zeolite may be any acidic zeolite. Some suitable acidic zeolites may include, but are not limited to MFI, MAZ, MEL, MTW, MEI, EMT, TON, MTT, FER, MRE, MFS, DDR, EWT, BET, USY, NES, EMM, MWW, MOR, and MSE, for example. Some specific zeolites may include, without limitation, ZSM-3, ZSM-4, ZSM-5, ZSM-11, ZSM-12, ZSM-18, ZSM-20 ZSM-22, ZSM-23, ZSM-35, ZSM-48, ZSM-57, ZSM-58, EMM-10, EMM-34, zeolite beta, zeolite Y, ultrastable Y (USY), dealuminized Y, mordenite, NU-87, MCM-22, MCM-68, PSH-3, SSZ-25, MCM-36, MCM-49, MCM-56, UZM-14, and combinations thereof. In some examples, the additional zeolite may have channels defined by 10 or more tetrahedral atoms. The additional zeolite may be present in any suitable amount in the catalyst. For example, the additional zeolite material may be present in an amount of about 1 wt. % to about 90 wt. % by weight of the catalyst. Alternatively, the additional zeolite may be present in an amount of about 1 wt. % to about 10 wt. %, about 10% to about 30 wt. %, about 30 wt. % about 50 wt. %, about 50 wt. % to about 70 wt. %, about 70 wt. % to about 90 wt. %, or any ranges therebetween.

The catalyst may further include a molecular sieve. Some molecular sieves may include, but are not limited to MFI, MAZ, MEL, MTW, MEI, EMT, TON, MTT, FER, MRE, MFS, DDR, EWT, BET, USY, and NES, for example. Some specific zeolites may include, without limitation ZSM-5, ZSM-11, ZSM-22, ZSM-23, ZSM-35, ZSM-48, ZSM-57, ZSM-58, and EMM-34. The molecular sieves may have any particle size suitable for a particular application. The molecular sieve may be present in any suitable amount in the catalyst. For example, the molecular sieve material may be present in an amount of about 1 wt. % to about 90 wt. % by weight of the catalyst. Alternatively, the molecular sieve may be present in an amount of about 1 wt. % to about 10 wt. %, about 10% to about 30 wt. %, about 30 wt. % about 50 wt. %, about 50 wt. % to about 70 wt. %, about 70 wt. % to about 90 wt. %, or any ranges there between.

The catalyst may further include binder or matrix material that may composite or otherwise bind together the individual components of the catalyst. Such materials may include active and inactive materials and synthetic or naturally occurring zeolites, as well as inorganic materials such as clays, silica and/or metal oxides such as alumina. The inorganic material may be either naturally occurring, or in the form of gelatinous precipitates or gels including mixtures of silica and metal oxides. Use of a binder or matrix material which itself is catalytically active, may change the conversion and/or selectivity of the catalyst composition. Inactive materials suitably serve as diluents to control the amount of conversion so that transalkylated products may be obtained without employing other means for controlling the rate of reaction. These catalytically active or inactive materials may include, for example, naturally occurring clays, e.g. bentonite and kaolin, to improve the crush strength of the catalyst composition under commercial operating conditions.

Naturally occurring clays that can be composited with the microporous material and additional zeolite may include clays from the montmorillonite and kaolin family, for example. The montmorillonite and kaolin families include the subbentonites, and the kaolins commonly known as Dixie, McNamee, Georgia and Florida clays or others in which the main mineral constituent is halloysite, kaolinite, dickite, nacrite or anauxite. Such clays may be used in the raw state as originally mined or initially subjected to calcination, acid treatment or chemical modification.

In addition to the foregoing materials, the catalyst may include a binder material, such as an inorganic oxide selected from the group consisting of silica, alumina, zirconia, titania, thoria, beryllia, magnesia, and combinations thereof, such as silica-alumina, silica-magnesia, silica-zirconia, silica-thoria, silica-beryllia, silica-titania, as well as ternary compositions such as silica-alumina-thoria, silica-alumina-zirconia, silica-alumina-magnesia and silica-magnesia-zirconia. It may also be advantageous to provide at least a part of the foregoing porous matrix binder material in colloidal form so as to facilitate extrusion of the catalyst composition. In some examples, microporous material and additional zeolite may be admixed with the binder or matrix material so that the first catalyst composition contains the binder or matrix material in an amount ranging from about 1 wt. % to about 90 wt. % by weight of the catalyst. Alternatively, the binder or matrix material may be present in an amount of about 1 wt. % to about 10 wt. %, about 10% to about 30 wt. %, about 30 wt. % about 50 wt. %, about 50 wt. % to about 70 wt. %, about 70 wt. % to about 90 wt. %, or any ranges therebetween.

As discussed above, the catalyst may include a microporous material with a metal constrained within cages or channels of the microporous material. The metal containing microporous material may be prepared by any suitable method such as by co-crystallization, exchanged into the microporous material, impregnated therein, or mixed with the microporous material and binder. In some examples the metal components may be impregnated in or on the microporous material by treating the microporous material with a solution containing elements from groups 6 to 12. Platinum may be added to the microporous material by contacting the microporous material with a solution containing a platinum metal-containing ion. Suitable platinum compounds for impregnating the microporous material with platinum include chloroplatinic acid, platinous chloride and various compounds containing the platinum ammine complex, such as $Pt(NH_3)_4Cl_2H_2O$, nitrate and hydroxides. After incorporation of the metal components, the microporous material may be dried by heating at a temperature of 65° C. to 160° C., typically 110° C. to 143° C., for at least 1 minute and generally not longer than 24 hours, at pressures ranging from 100 to 200 kPa-a. Thereafter, the microporous material may be calcined in a stream of dry gas, such as air or nitrogen, at temperatures of from 260° C. to 650° C. for 1 to 20 hours. Calcination is typically conducted at pressures ranging from 100 to 300 kPa-a.

Accordingly, the preceding description describes catalyst system for converting C9+ aromatics to lighter aromatics. The systems and methods disclosed herein may include any of the various features disclosed herein, including one or more of the following embodiments.

Embodiment 1 A catalyst comprising: a metallic function derived from a metal constrained within cages and/or channels of a microporous material, wherein the cages and/or channels of the microporous material are defined by 8 tetrahedral atoms or fewer; and an acidic function derived from an additional zeolite having cages and/or channels defined by 10 or more tetrahedral atoms, wherein the microporous material providing the metallic function and additional zeolite providing the acidic function are coupled by a binder.

Embodiment 2. The catalyst of embodiment 1 wherein the microporous material is selected from the group consisting of AEI, AFT, AFX, CHA, CDO, DDR, EDI, ERI, IHW, ITE, ITQ-55, ITW, KFI, MER, MTF, MWF, LEV, LTA, PAU, PWY, RHO, SOD, SFW, UFI, and combinations thereof.

Embodiment 3. The catalyst of any of embodiments 1-2 wherein the metal is selected from the group consisting of platinum, palladium, gallium, iridium, rhenium, copper, silver, gold, ruthenium, rhodium, iron, tungsten, molybdenum, cobalt, nickel, and combinations thereof.

Embodiment 4. The catalyst of any of embodiments 1-3 wherein at least 80% by weight of the metal is constrained within the cages and/or channels of the microporous material wherein at least 80% by weight of the metal is constrained within cages or channels of a microporous material.

Embodiment 5. The catalyst of any of embodiments 1-4 wherein the additional zeolite is selected from the group consisting of MFI, MAZ, MEL, MTW, MEI, EMT, TON, MTT, FER, MRE, MFS, DDR, EWT, BET, USY, NES, EMM, MWW, MOR, MSE, and combinations thereof.

Embodiment 6. The catalyst of any of embodiments 1-5 wherein the microporous material comprises chabazite, wherein the metal comprises platinum, and wherein the additional zeolite comprises at least one of MFI, MEL, or MOR.

Embodiment 7. The catalyst of any of embodiments 1-6 further comprising a binder selected from the group consisting of an alumina binder, a silica binder, and combinations thereof, and wherein the binder is present in an amount of about 1 wt. % to about 20 wt. % by weight of the catalyst.

Embodiment 8. A method comprising: introducing a feed comprising hydrogen, toluene, and C9+ aromatic hydrocarbons into a reactor, wherein at least a portion of the C9+ aromatic hydrocarbons comprise a C2+ alkyl group; and contacting the feed with a catalyst comprising: a metallic function derived from a metal constrained within cages and/or channels of a microporous material, wherein the cages and/or channels of the microporous material are defined by 8 tetrahedral atoms or fewer; and an acidic function derived from an additional zeolite having cages and/or channels defined by 10 or more tetrahedral atoms, wherein the microporous material providing the metallic function and additional zeolite providing the acidic function are coupled by a binder, wherein the catalyst is effective to dealkylate at least a portion of the C9+ aromatic hydrocarbons comprising a C2+ alkyl group to generate a corresponding olefin and C9+ aromatic hydrocarbon and hydrogenate at least a portion of the corresponding olefin to form a corresponding alkane.

Embodiment 9. The method of embodiment 8 wherein the microporous material is selected from the group consisting of AEI, AFT, AFX, CHA, CDO, DDR, EDI, ERI, IHW, ITE, ITQ-55, ITW, KFI, MER, MTF, MWF, LEV, LTA, PAU, PWY, RHO, SOD, SFW, UFI, and combinations thereof.

Embodiment 10. The method of any of embodiments 8-9 wherein the metal is selected from the group consisting of platinum, palladium, gallium, iridium, rhenium, copper, silver, gold, ruthenium, rhodium, iron, tungsten, molybdenum, cobalt, nickel, and combinations thereof.

Embodiment 11. The method of any of embodiments 8-10 wherein the additional zeolite is selected from the group consisting of MFI, MAZ, MEL, MTW, MEI, EMT, TON, MTT, FER, MRE, MFS, DDR, EWT, BET, USY, NES, EMM, MWW, MOR, MSE, and combinations thereof.

Embodiment 12. The method of any of embodiments 8-11 wherein the catalyst is further effective to transalkylate the toluene and the C9+ aromatic hydrocarbon to form xylene.

Embodiment 13. The method of any of embodiments 8-12 wherein the microporous material comprises chabazite, wherein the metal comprises platinum, and wherein the additional zeolite comprises at least one of MFI, MEL, or MOR.

Embodiment 14. A method comprising: contacting an aromatic hydrocarbon feed with a catalyst composition comprising: a metallic function derived from a metal constrained within cages or channels of a microporous material, wherein the cages or channels of the microporous material are defined by 8 tetrahedral atoms or fewer; and an acidic function derived from an additional zeolite having channels defined by 10 or more tetrahedral atoms, wherein the microporous material providing the metallic function and additional zeolite providing the acidic function are coupled by a binder, wherein the aromatic hydrocarbon feed comprises toluene, and C9+ aromatic hydrocarbons, and wherein at least a portion of the C9+ aromatic hydrocarbons comprise a C2+ alkyl group; dealkylating at least a portion of the C9+ aromatic hydrocarbon comprising C2+ alkyl groups to form a corresponding C2+ olefin and C9+ aromatic hydrocarbon; saturating at least a portion of the C2+ olefin formed to produce a corresponding C2+ alkane; and transalkylating at least a portion of the C9+ aromatic hydrocarbon with the toluene to form xylene.

Embodiment 15. The method of embodiment 14 wherein the microporous material is selected from the group consisting of AEI, AFT, AFX, CHA, CDO, DDR, EDI, ERI, IHW, ITE, ITQ-55, ITW, KFI, MER, MTF, MWF, LEV, LTA, PAU, PWY, RHO, SOD, SFW, UFI, and combinations thereof.

Embodiment 16. The method of any of embodiments 14-15 wherein the metal is selected from the group consisting of platinum, palladium, gallium, iridium, rhenium, copper, silver, gold, ruthenium, rhodium, iron, tungsten, molybdenum, cobalt, nickel, and combinations thereof.

Embodiment 17. The method of any of embodiments 14-16 wherein the additional zeolite is selected from the group consisting of MFI, MAZ, MEL, MTW, MEI, EMT, TON, MTT, FER, MRE, MFS, DDR, EWT, BET, USY, NES, EMM, MWW, MOR, MSE, and combinations thereof.

Embodiment 18. The method of any of embodiments 14-17 wherein the microporous material comprises chabazite, wherein the metal comprises platinum, and wherein the additional zeolite comprises at least one of MFI, MEL, or MOR.

Embodiment 19. The method of any of embodiments 14-18 further comprising separating at least a portion of the xylene to form a xylene rich stream.

Embodiment 20. The method of any of embodiments 14-19 wherein the aromatic hydrocarbon feed further comprises hydrogen.

EXAMPLES

To facilitate a better understanding of the present invention, the following examples of certain aspects of some embodiments are given. In no way should the following examples be read to limit, or define, the entire scope of the invention.

Example 1

In this example, a noble metal encapsulated in small pore chabazite (CHA) was prepared. First, 800 mg of sodium hydroxide was dissolved in 6.9 g of water. Then, 86 mg of an 8 wt. % aqueous solution of chloroplatinic acid ($H_2PtCl_6$ 37.5 wt. % Pt basis) and 52 mg of 3-mercaptopropyl trimethoxysilane (TMSH) were added to the aqueous solution of sodium hydroxide and stirred for about 30 minutes. Afterwards, 13.04 g of an aqueous solution of N,N,N-trimethyl-l-adamantammonium hydroxide (TMAdA) 16.2 wt. % in water was added and maintained under stirring for about 15 minutes. After about 15 minutes, 293 mg of aluminum hydroxide (58 wt %) was added, and the resultant mixture kept under stirring at about 80° C. for about 30 minutes. Thereafter, 3 g of colloidal silica was introduced to the mixture and maintained under stirring at 80° C. for 30 minutes. The final gel composition was found to be $SiO_2$: 0.033 $Al_2O_3$: 0.00033 Pt:0.005 TMSH:0.2 TMAdA:0.4 NaOH:20 H2O. The gel was transferred to an autoclave with a PTFE liner, and heated at about 90° C. for a period of about 7 days, and later, at about 160° C. for about 2 days under dynamic conditions. The sample after hydrothermal crystallization was filtered and washed with abundant distilled water, and finally dried at 100° C. The Pt-containing CHA was calcined at 550° C. in air in order to remove the organic moieties included inside the microporous material during the crystallization process. The calcined sample was treated with $H_2$ at 400° C. for 2 hours.

Example 2

In this example, an EMM-34 zeolite was prepared. A mixture was prepared from 9300 g of water, 804 g of tetraethylammonium bromide (TEABr) (50 wt. % solution), 2750 g of silica, 584 g of sodium aluminate solution (45 wt. %), and 612 g of 50 wt. % sodium hydroxide solution. Thereafter 30 g of mordenite seeds were added to the mixture. The mixture was reacted at about 143° C. in an autoclave with stirring for about 72 hours. The product was filtered, washed with deionized water, and dried at about 121° C. The as-synthesized crystals were calcined in nitrogen at about 538° C. and converted to the hydrogen form by three ion exchanges with ammonium nitrate solution at room temperature, followed by drying at about 121° C. and calcination at about 540° C. for about 6 hours. The resulting EMM-34 was found to have an $SiO_2/Al_2O_3$ molar ratio of about 21, a surface area of 637 m²/g, and a meso-pore surface area of 56 m²/g.

Example 3

In this example, a ZSM-11 zeolite was prepared. A mixture was prepared from 8250 g of water, 1540 g of tetra-n-butylammonium bromide (TBABr) 50 wt. % solution, 2750 g of silica, 1010 g of aluminum sulfate 47 wt. % solution, 880 g of 50 wt. % sodium hydroxide solution, and 30 g of ZSM-11 seed crystal. The mixture was reacted in an autoclave at 121° C. with stirring for about 72 hours. The resultant product was filtered, washed with deinioned water and dried at 121° C. The as-synthesized crystals were converted into the hydrogen form by three ion exchanges with ammonium nitrate solution at room temperature, followed by drying at 120° C. and calcination at 540° C. to for 6 hours. The resulting ZSM-11 crystals were found to have an $SiO_2/Al_2O_3$ molar ratio of about 50, and a total surface area of (SA)/(micropore SA+mesopore SA) of 481/(364+117) m²/g.

Example 4

In this example, a ZSM-5 zeolite was prepared. A first mixture was prepared from 22.0 grams of $SiO_2$ partially dissolved in 100 mL of 2.18 N tetrapropylammonium hydroxide by heating to a temperature of about 100° C. Then, a second mixture of 3.19 grams of $NaAlO_2$ (analyzed to include 42.0 wt. % $Al_2O_3$, 30.9 wt. % $Na_2O$, 27.1 wt. % $H_2O$) was dissolved in 53.8 ml $H_2O$. The first mixture and the second mixture were mixed and found to have the following composition: 0.382 mole $SiO_2$, 0.0131 mole $Al_2O_3$, 0.0159 mole $Na_2O$, 0.118 mole $CH_3CH_2CH_2NO$, and 6.30 moles $H_2O$. The combined mixture was placed in a borosilicate lined autoclave and heated at about 150° C. for about six days. The resultant solid product was cooled to room temperature, removed, filtered, washed with 1 liter of $H_2O$, and dried at about 110° C. The as-synthesized crystals were pre-calcined in nitrogen at 538° C. and then converted to the hydrogen form by three ion exchanges with ammonium nitrate solution at room temperature, followed by drying at about 121° C. and about 540° C. for about 6 hours.

Example 5

In this example, an EMM-34/ZSM-11/Alumina catalyst support was prepared. A catalyst support powder was prepared by mixing 44 parts of EMM-34 crystal from Example 2, 36 pats of ZSM-11 from Example 3, and 20 parts alumina in a muller. A sufficient amount of water was added to form an extrudable paste. The mixture of EMM-34, ZSM-11, alumina, and water was extruded as ¹/₁₆ inch (1.5875 mm) cylinders and then dried in an oven at 121° C. overnight. The dried extrudates were precalcined in nitrogen at 538° C. to decompose and remove the organic template. The precalcined extrudates were then humidified with saturated air at ambient conditions for 1 hour. After humidification, the extrudates were exchanged with 1 N ammonium nitrate to remove sodium. The extrudates were then washed with deionized water prior to drying at 121° C. for at least 4 hrs. The resulting material was then calcined in air at 538° C.

Example 6

In this example, a first catalyst is prepared by adding Pt encapsulated with CHA to the support of Example 5. 75 parts of the 44/36/20 EMM-34/ZSM-11/Alumina catalyst from Example 5 were mixed with 25 parts of 0.2 wt. % Pt encapsulated in small pore CHA from Example 1 in a rotary mill, pressed, and sized to 1000-1410 μm.

Example 7

In this example, a second catalyst is prepared. First, 44 parts of EMM-34 crystal from Example 2, 36 parts of ZSM-11 from Example 3, and 20 parts alumina were mixed in a muller. An aqueous solution of tetraammine platinum chloride and tin(II) chloride dehydrate in water was added to the muller prior to forming to a target loading on the final extrudates of 0.03 w.t % Pt and 0.11 wt. % Sn. The mixture of EMM-34, ZSM-11, alumina, and water was extruded into ¹/₁₆ inch (1.5875 mm) cylinders and then dried in an oven at 121° C. overnight. The dried extrudates were precalcined in nitrogen at 538° C. extrudates was then washed with deionized water prior to drying at 121° C. for at least 4 hrs. The resulting material was then calcined in air at 538° C.

Example 8

In this example, a third catalyst is prepared. First, 44 parts of EMM-34 crystal from Example 2, 36 parts of ZSM-11 from Example 3, and 20 parts silica were mixed in a muller. An aqueous solution of solution of tetraammine platinum chloride and tin(II) chloride dehydrate in water was added to the muller prior to forming to a target loading on the final extrudates of 0.03 wt. % Pt and 0.11 wt. % Sn. The mixture of EMM-34, ZSM-11, silica, and water was extruded into ¹/₁₆ inch (1.5875 mm) cylinders and then dried in an oven at 121° C. overnight. The dried extrudates were precalcined in nitrogen at 538° C. to decompose and remove the organic template. The precalcined extrudates were then humidified with saturated air at ambient conditions for one hour. After humidification, the extrudates were exchanged with 1 N ammonium nitrate to remove sodium. The extrudates were then washed with deionized water prior to drying at 121° C. for at least 4 hrs. The resulting material was then calcined in air at 538° C.

Example 9

In this example, a fourth catalyst is prepared. 50 parts of EMM-34 crystal from Example 2 were mixed with 20 parts of ZSM-5 crystal from Example 4 and 30 parts alumina in a muller. An aqueous solution of tetraammine platinum chloride and gallium(III) Nitrate was added to the muller prior to forming to a target loading on the final extrudates of 0.03 wt. % Pt and 0.032 wt. % Ga. The mixture of EMM-34, ZSM-5, alumina, and water was extruded into 1/16 inch (1.5875 mm) cylinders and then dried on a conveyor convection oven at 121° C. for several hours. The dried extrudates were precalcined in nitrogen at 538° C. to decompose and remove the organic template. The precalcined extrudates was then humidified with saturated air at ambient conditions for one hour. After humidification, the extrudates were exchanged with 1 N ammonium nitrate to remove sodium. The extrudates were then washed with deionized water prior to drying at 121° C. for at least 4 hrs. The resulting material was then calcined in air at 538° C.

Example 10

In this example, the catalysts prepared in the previous Examples will be tested. Examples 6-9 were evaluated in a parallel microunits using a blend of 60% C9+ heavy aromatic feed with 40% of Toluene which was co-fed with hydrogen. The feed composition is shown in Table 1. First, 2 grams of each of the catalysts prepared in examples 6-9 were sized to 14-18 mesh (1000-1410 µm) and loaded into a reactor with equal parts quartz on a weight basis. The catalysts were first activated by heating up to 400° C. in hydrogen and for 2 hours. The catalysts were then cooled to 350° C. at which time the feed blend was introduced (unless otherwise noted). Reactor pressure was 390 psig (26.9 bar) and the heavy aromatic feed to hydrogen ratio was 2. Product composition exiting the reactors was analyzed using an FID-GC following component separation on a 60 m DB-1 column. The results of the experiment are shown in Tables 2 and 3. In Table 2, the ring loss was calculated by Equation 1.

$$\text{Ring Loss (\%)} = \frac{1 - \text{Sum Mol Ring Effluent}}{\text{Sum Mol Ring Effluent}} \quad \text{Equation 1}$$

TABLE 1

| Component | Mole Fraction |
| --- | --- |
| Toluene | 41.4 |
| N-propylbenzene | 3.5 |
| 1-methyl-3-ethylbenzene | 11.7 |
| 1-methyl-4-ethylbenzene | 5.0 |
| 1,3,5-trimethyl-benzene | 6.0 |
| 1-methyl-2-ethylbenzene | 4.5 |
| 1,2,4-trimethylbenzene | 17.7 |
| 1,2,3-trimethylbenzene | 2.4 |

TABLE 2

| Catalyst | C6+ non-aromatics (wt. %) | Ring Loss (%) | Ethane/Ethylene ratio |
| --- | --- | --- | --- |
| Example 6 | 0.06 | 1.8 | 2865 |
| Example 7 | 0.11 | 2.5 | 1675 |
| Example 8 | 0.08 | 2.4 | 801 |
| Example 9 | 0.14 | 2.6 | 450 |

TABLE 3

| Catalyst | Ethyl-Aromatic Conv. (%) | Ethane Prod. (wt. %) | Propyl Aromatic Conv. (%) | Propane Prod. (wt. %) | *Propyl-aromatic conv. (%) | *Propane Prod (wt. %) | Isobutane Prod. (wt. %) | Isopentane Prod (wt. %) |
| --- | --- | --- | --- | --- | --- | --- | --- | --- |
| Example 6 | 62 | 3.4 | 99.5 | 2.4 | 99.5 | 2.8 | 0.3 | 0.1 |
| Example 7 | 62 | 3 | 99.5 | 2.9 | 99.3 | 4 | 0.8 | 0.3 |
| Example 8 | 72 | 3.8 | 99.6 | 2.7 | 99.4 | 4.1 | 0.7 | 0.2 |
| Example 9 | 53 | 2.2 | 99.3 | 2.9 | 99 | 4.4 | 0.9 | 0.3 |

*These reactions were carried out at 400° C.

The above example demonstrates that the catalyst from Example 6 comprising the metal encapsulated small pore CHA has the lowest C6+ non-aromatics (related to high benzene purity) compared to the catalyst from Example 7-9. As bulkier hydrocarbons (e.g. aromatics) are not able to diffuse into the pores of the small pore zeolite (e.g. CHA), where the metal function is located, no ring saturation occurs (hence low C6+ non-aromatics, shown in Table 1). Similarly, the ring loss for the catalyst from Example 6 is lower compared to the other catalysts from Example 7-9. In addition, the ethane/ethylene ratio for the catalyst from Example 6 is 1.7 times higher than the catalyst from Example 7, 3.5 times higher than the catalyst from 3.5, and 6.3 times higher than the catalyst from Example 9, as there is no second metal in the catalyst composition of the catalyst from Example 6 that negatively affects the noble metal hydrogenation activity, as it is the case with catalysts from Examples 6-9. Thus, the catalyst from Example 6 selectively hydrogenates ethylene (e.g. from ethyltoluene dealkylation) in the presence of aromatics, while preserving the high hydrogenation activity of the noble metal.

It was observed that the ethyl-aromatic conversion for the catalyst from Example 6 comprising of the metal encapsulated small pore CHA is comparable with that of the catalyst from Example 7, higher than that of the catalyst from Example 9, and lower compared to the catalyst from Example 8. The trends in ethyl-aromatic conversion are consistent with the ethane production trends where the higher the ethyl-aromatic conversion observed, the higher the ethane production observed. The propyl-aromatic conversion for the catalyst from Example 6 is comparable to that of the catalyst from Example 7-9. It was observed that the catalyst from Example 6 produced less propane than the catalyst from Examples 7-9 at higher propyl-aromatic conversion. Propane production was further improved at higher temperature, where the catalyst from Example 6 produced about ⅔ of the propane than the catalysts from Example 7-8 produced, while high propyl-aromatic conversion is maintained. In addition, it was observed that isobutane production from the catalyst from Example 6 is lower than catalysts from Example 7-9. These results are consistent with the notion that the metal encapsulated Cat from Example 6 has considerably less hydrocarbon cracking than the catalysts from Example 7-9.

While the invention has been described with respect to a number of embodiments and examples, those skilled in the art, having benefit of this disclosure, will appreciate that other embodiments can be devised which do not depart from the scope and spirit of the invention as disclosed herein. Although individual embodiments are discussed, the invention covers all combinations of all those embodiments.

While compositions, methods, and processes are described herein in terms of "comprising," "containing," "having," or "including" various components or steps, the compositions and methods can also "consist essentially of" or "consist of" the various components and steps. The phrases, unless otherwise specified, "consists essentially of" and "consisting essentially of" do not exclude the presence of other steps, elements, or materials, whether or not, specifically mentioned in this specification, so long as such steps, elements, or materials, do not affect the basic and novel characteristics of the invention, additionally, they do not exclude impurities and variances normally associated with the elements and materials used.

All numerical values within the detailed description and the claims herein modified by "about" or "approximately" with respect the indicated value are intended to take into account experimental error and variations that would be expected by a person having ordinary skill in the art.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited.

What is claimed is:

1. A catalyst comprising:
   a metallic function derived from a metal constrained within cages and/or channels of a microporous material, wherein the cages and/or channels of the microporous material are defined by 8 tetrahedral atoms or fewer; and
   an acidic function derived from an additional zeolite having cages and/or channels defined by 10 or more tetrahedral atoms,
   wherein the metal containing microporous material and the additional zeolite providing the acidic function are coupled by a binder.

2. The catalyst of claim 1, wherein the microporous material is selected from the group consisting of AEI, AFT, AFX, CHA, CDO, DDR, EDI, ERI, IHW, ITE, ITQ-55, ITW, KFI, MER, MTF, MWF, LEV, LTA, PAU, PWY, RHO, SOD, SFW, UFI, and combinations thereof.

3. The catalyst of claim 1, wherein the metal is selected from the group consisting of platinum, palladium, gallium, iridium, rhenium, copper, silver, gold, ruthenium, rhodium, iron, tungsten, molybdenum, cobalt, nickel, and combinations thereof.

4. The catalyst of claim 1, wherein at least 80% by weight of the metal is constrained within the cages and/or channels of the microporous material.

5. The catalyst of claim 1, wherein the additional zeolite is selected from the group consisting of MFI, MAZ, MEL, MTW, MEI, EMT, TON, MTT, FER, MRE, MFS, DDR, EWT, BET, USY, NES, EMM, MWW, MOR, MSE, and combinations thereof.

6. The catalyst of claim 1, wherein the microporous material comprises chabazite, wherein the metal comprises platinum, and wherein the additional zeolite comprises at least one of MFI, MEL, or MOR.

7. The catalyst of claim 1, wherein the binder is selected from the group consisting of an alumina binder, a silica binder, and combinations thereof, and wherein the binder is present in an amount of about 1 wt. % to about 20 wt. % by weight of the catalyst.

8. The catalyst of claim 1, wherein the metal is present in an amount between about 0.001 wt % and 5 wt % by weight of the catalyst.

9. The catalyst of claim 1, wherein the microporous material is present in an amount of about 1 wt % to about 90 wt % by weight of the catalyst.

10. The catalyst of claim 1, wherein the additional zeolite is present in an amount of about 1 wt % to about 90 wt % by weight of the catalyst.

11. The catalyst of claim 1, wherein the additional zeolite includes at least one of ZSM-5, ZSM-11, and EMM-34.

12. The catalyst of claim 1, wherein the metal containing microporous material is prepared by co-crystallization, exchange, impregnation, or mixing.

13. A method comprising:
    introducing a feed comprising hydrogen, toluene, and C9+aromatic hydrocarbons into a reactor, wherein at least a portion of the C9+aromatic hydrocarbons comprise a C2+alkyl group; and
    contacting the feed with the catalyst of claim 1,
    wherein the catalyst is effective to dealkylate at least a portion of the C9+aromatic hydrocarbons comprising a C2+alkyl group to generate a corresponding olefin and C9+aromatic hydrocarbon and hydrogenate at least a portion of the corresponding olefin to form a corresponding alkane.

14. The method of claim 13, wherein the microporous material is selected from the group consisting of AEI, AFT, AFX, CHA, CDO, DDR, EDI, ERI, IHW, ITE, ITQ-55, ITW, KFI, MER, MTF, MWF, LEV, LTA, PAU, PWY, RHO, SOD, SFW, UFI, and combinations thereof.

15. The method of claim 13, wherein the metal is selected from the group consisting of platinum, palladium, gallium, iridium, rhenium, copper, silver, gold, ruthenium, rhodium, iron, tungsten, molybdenum, cobalt, nickel, and combinations thereof.

16. The method of claim 13, wherein the additional zeolite is selected from the group consisting of MFI, MAZ, MEL, MTW, MEI, EMT, TON, MTT, FER, MRE, MFS, DDR, EWT, BET, USY, NES, EMM, MWW, MOR, MSE, and combinations thereof.

17. The method of claim 13, wherein the catalyst is further effective to transalkylate the toluene and the C9+aromatic hydrocarbon to form xylene.

18. The method of claim 13, wherein the microporous material comprises chabazite, wherein the metal comprises platinum, and wherein the additional zeolite comprises at least one of MFI, MEL, or MOR.

19. The method of claim 13, further comprising:
    dealkylating at least a portion of the C9+aromatic hydrocarbon comprising C2+alkyl groups to form a corresponding C2+olefin and C9+aromatic hydrocarbon;
    saturating at least a portion of the C2+olefin formed to produce a corresponding C2+alkane; and
    transalkylating at least a portion of the C9+aromatic hydrocarbon with the toluene to form xylene.

20. The method of claim 19, wherein the microporous material is selected from the group consisting of AEI, AFT, AFX, CHA, CDO, DDR, EDI, ERI, IHW, ITE, ITQ-55, ITW, KFI, MER, MTF, MWF, LEV, LTA, PAU, PWY, RHO, SOD, SFW, UFI, and combinations thereof.

21. The method of claim 19, wherein the metal is selected from the group consisting of platinum, palladium, gallium, iridium, rhenium, copper, silver, gold, ruthenium, rhodium, iron, tungsten, molybdenum, cobalt, nickel, and combinations thereof.

22. The method of claim 19, wherein the additional zeolite is selected from the group consisting of MFI, MAZ, MEL, MTW, MEI, EMT, TON, MTT, FER, MRE, MFS, DDR, EWT, BET, USY, NES, EMM, MWW, MOR, MSE, and combinations thereof.

23. The method of claim 19, wherein the microporous material comprises chabazite, wherein the metal comprises platinum, and wherein the additional zeolite comprises at least one of MFI, MEL, or MOR.

24. The method of claim 19, further comprising separating at least a portion of the xylene to form a xylene rich stream.

* * * * *